United States Patent [19]

Gajdos

[11] Patent Number: 4,906,813

[45] Date of Patent: Mar. 6, 1990

[54] DEVICE AND PROCESS FOR MARKING MOLDED ITEMS AND TABLETS WITH LASER BEAMS

[75] Inventor: Benedikt Gajdos, Cologne, Fed. Rep. of Germany

[73] Assignee: A. Nattermann & CIE GmbH, Cologne, Fed. Rep. of Germany

[21] Appl. No.: 228,912

[22] PCT Filed: Jul. 31, 1987

[86] PCT No.: PCT/EP87/00420

§ 371 Date: Jul. 28, 1988

§ 102(e) Date: Jul. 28, 1988

[87] PCT Pub. No.: WO88/00884

PCT Pub. Date: Feb. 11, 1988

[30] Foreign Application Priority Data

Aug. 2, 1986 [DE] Fed. Rep. of Germany ....... 3626249
Aug. 2, 1986 [DE] Fed. Rep. of Germany ....... 3626250

[51] Int. Cl.$^4$ .............................................. B23K 26/00
[52] U.S. Cl. ............................ 219/121.68; 219/121.69
[58] Field of Search ...................... 219/121.68, 121.69

[56] References Cited

U.S. PATENT DOCUMENTS

| T 903,014 | 10/1972 | Dempski | 219/121.85 |
| 3,657,510 | 4/1972 | Rothrock | 219/121.61 |
| 4,219,721 | 8/1980 | Kamen et al. | 219/121.69 X |
| 4,323,317 | 4/1982 | Hasegawa | 219/121.68 |
| 4,564,737 | 1/1986 | Burke et al. | 219/121.68 |
| 4,578,329 | 3/1986 | Holsappel | 219/121.68 X |

FOREIGN PATENT DOCUMENTS

| 378646 | 10/1907 | France . |
| 61-5988 | 1/1986 | Japan . |
| 62-164610-A | 7/1987 | Japan . |

OTHER PUBLICATIONS

*Modern Plastics International*, vol. 11 (1981), Oct., No. 10, Lausanne, Switzerland, pp. 21-22.

Primary Examiner—C. L. Albritton
Attorney, Agent, or Firm—Burns, Doane, Swecker & Mathis

[57] ABSTRACT

Process and device for applying markings (9) and/or providing break notches on moulded items or tablets (4) by means of laser beams. The installation (16) which produces the laser beam (3) is arranged on a tablet-producing press, to which it is functionally connected by synchronization systems (18). A deflection system (17) is arranged on the die support (5) of the press in order to deflect the laser beam (3) onto the surface of the moulded item or tablet (4). The laser (16) is provided with an optical system (15) having interchangeable masks provided with openings through which the laser beam passes (3).

10 Claims, 6 Drawing Sheets

DEVICE AND PROCESS FOR MARKING MOLDED ITEMS AND TABLETS WITH LASER BEAMS

BACKGROUND OF THE INVENTION

1. Field of the Invention

The invention relates to a process and a device for marking molded items, tablets with monochrome or polychrome symbols, letters, numbers or break notches by applying the desired markings with the aid of a pulsed laser beam, the laser being arranged directly in a tablet-producing press.

The marking of solid forms of drugs is a necessity, in order to prevent the risk of confusion during manufacture and distribution, and to enable a rapid identification, for example in connection with cases of poisoning. It is for this reason, for example, that diverse recommendations or statutory requirements (GMP, among others) exist in many countries of the World. The manufacturers of solid drugs are dutybound to manufacture the latter in such a way that the risk of confusion is minimal as early as during the process of manufacture. Use of the above markings could further increase safety in this area. Monochrome or polychrome marking of molded items and tablets is possible by more than one process.

2. Description of the Related Art

A known process for the marking of tablets is the dying of the pressing mixture and/or stamping with stamping tools specially manufactured for the purpose. The disadvantages of this manufacturing process are a higher expenditure on development and more complicated formulae because of the dye distribution and/or stamping. Additional problems are occasioned by legal restrictions on the use of dyes, which are not always internationally uniform, and by the machine performance, which, due to the use of stamping tools, is not always as desired. In addition, depending on the stamping, the stamping tools are much more expensive than pressing tools in the absence of stamping. In addition, the formulae pressed with a stamping punch require a more intensive, ie. also a more expensive development, and the use of special auxiliary materials, because with the use of stamping punches, tablet formulae which can be pressed without a problem using normal, curved or plane punches can give rise to considerable difficulties depending on the nature of the stamping. Also in use are a number of processes for printed markings and, for example, an ink marking process, the so-called ink-jet printing system, is described in U.S. Pat. No. 4,548,825. In all these processes, the tablets are printed in a specially developed apparatus only once they have been manufactured, which means that the cost of the preparation is substantially increased. Moreover, during manufacture or intermediate storage, the risk of confusion mentioned above could well always be there. Another common process is the coating of tablets with films of different colors, the advantage being that all stampings, break grooves, etc. remain visible. The tablets to be film-coated must have a certain minimal curvature, which is important for the rolling movement in the coating apparatus. The disadvantage is that with curvature or additional stamping, the tablets become more difficult to press. In general, the film tablets require a considerably higher expenditure on raw material and development than does the tablet marking by dyeing the pressing mixture. It is also possible to sugar-coat tablets, but here, too, only biconvex molded items are capable of being sugar-coated well and the stampings and break grooves on the molded item or dragee core are covered over by the dragee coating, and so do not remain visible. Disadvantages are the long manufacturing period and the associated uneconomic nature of the manufacture of dragees.

The marking of tablets with the aid of lasers is fundamentally known (U.S. Pat. No. 3,657,510) and Defensive Publication T 903,014). However, both processes lack a system for the exact alignment of the tablets to be marked.

Even assuming that such apparatuses already exist for use in the marking of tablets, there remains the intermediate storage of the tablets to be marked after pressing and thus the risk of confusing tablets of similar appearance before or during the marking process.

SUMMARY OF THE INVENTION

It is the object of the invention to organize the marking of molded items and tablets in a safer fashion and to exclude confusions and false markings.

This object is achieved by arranging the system which generates the laser beams, also known simply as the laser, on a tablet-producing press with which it forms a unit. The laser is arranged in such a way that the specially guided laser beam operates on the material to be marked either from the side or from above the tablet while it is still on the lower punch in the die, doing so directly after the pressing process or as the tablet is ejected or in a special tablet alignment. The achievement according to the invention is a process for applying markings and/or providing break notches on molded items or tablets by treating the surface with a laser beam, in which process the treatment takes place generally coterminously with ejection of the molded item or the tablet from the die of a tablet-producing press. Preferably, this comprises deflecting the laser beam onto the top of the molded item or the tablet. In another embodiment, the laser beam is deflected onto the side face of the molded item or of the tablet, and the the (sic) treatment is carried out at the moment at which the molded item is ejected from the die by the lower punch as far as above the upper edge of the former. In order to be able to apply different markings, the form of the marking is produced by a mask arranged in the laser beam and having openings in the form of the desired marking.

The invention also includes a device for applying markings and/or providing break notches on molded items or tablets by means of laser beams using an installation to generate a laser beam, an installation to generate a laser beam (sic) which is arranged on a tablet-producing press, to which it is functionally connected by synchronization systems, and a deflection system, which is arranged on the die support of the tablet-producing press in order to deflect the laser beam onto the surface of the molded item or tablet.

The installation for generating the laser beam is preferably a gas laser. The installation for generating the laser beam is provided with an optical system having interchangeable masks, through whose openings the laser beam passes. The deflection direction (sic) can be arranged and aligned by the side of the die support in such a way that the laser beam runs parallel to the surface of the die support in the direction of the vertical axis of the die. Alternatively, the deflection system is arranged and aligned at the side of the upper punch of the tablet-producing press in such a way that the laser beam strikes the top of the molded item or tablet before the center of the molded item or tablet has been displaced horizontally from the vertical axis of the die. If eccentric presses are used in place of rotary presses, it is preferred to provide systems to move the deflection system back and forth from a position by the side of the upper punch into a position above the die, in order to be able to apply the marking on the top of the molded item. It should be stressed in this connection that a special alignment device can be replaced by time synchronization of the laser employed with the tablet-producing press and the path followed by the tablet as dictated by the tablet-producing press.

The synchronization of the operating cycle of the tablet-producing press with the laser is such that the treatment of the surface of the molded item with the laser beam takes place after completion of the pressing process and the withdrawal of the upper punch from the die. Depending on the deflection of the laser beam, the latter strikes the top of the molded item while the latter is still located in the die, or while it is being ejected from the die, as long as the molded item is only being moved vertically, but not horizontally.

However, the synchronization can also be arranged so that an appropriately deflected and aligned laser beam strikes the side of the molded item immediately after vertical ejection from the die.

Apart from the various signs, letters etc. applied to the surface of the molded items, it is also possible to apply markings laterally onto the edges. Moreover, partial notches or break notches can be produced on tablets.

If molded items or tablets having different colored layers are treated with the laser beam for marking purposes, the different colored layers can be burned out layer by layer depending on the desired makeup of the marking as to color and pattern.

It follows that application of the system can replace the conventional marking of molded items by means of stamping tools, which offers considerable advantages, such as, for example, savings on stamping tools, since by changing the signs or lettering of the laser it is possible to use the same pressing tool to provide any number of preparations with a distinguishing mark, but also savings on development work for formulae, since the expensive formulae required for stamping tools are not necessary.

A commercial gas or solid-state laser can be arranged on the tablet-producing press, particular preference being given to carbon dioxide, excimer or YAG lasers. In this process the laser beam can be applied using two different methods (laser marking system). On the one hand, the laser beam can be guided through a mask, whose openings correspond to the signs to be reproduced. On the other hand, the laser beam is focused on the molded item or tablet to be marked and reproduces the desired signs with the aid of a computer program. The carefully focused laser beam, guided with the aid of, for example, glass fibers or mirrors onto the surface of the tablet, then forms the desired signs by melting, bleaching, vaporizing, oxidizing etc. the surface of the tablet. If necessary, the beam guide can be mobile and synchronized with the movement of the parts of the tablet-producing machine by, for example, a telescopic or swivelling movement. The laser beam is intensity-modulated, so that the focused laser energy writes or prints the word or symbol to be used onto the tablet. It should be emphasized in this connection that this technique is not confined to tablets, but can be applied to molded items of the most varied materials or compositions, such as, for example, molded items of any shape made from various plastics, metals and other pressable materials from the fields of chemistry, foodstuffs, electronics, inter alia, for example, control buttons, catalysts, ceramic components and the like.

A further advantage of the system according to the invention is the fact that by changing the laser computer program or the writing masks it is easy to interchange the symbols, letters or numbers to be stamped.

Additional advantages relate to an economic and efficient production, since the laser writing can be carried out with polished and unpolished tablets, be cause surface dust on tablets poses no problem in relation to the production of a clear inscription. It follows that the system is suitable for higher production speeds in a clean process, and can, in addition, be used for the marking of uneven, curved and otherwise shaped surfaces.

The arrangement of the system according to the invention will now be further described with the aid of the drawings.

DETAILED DESCRIPTION OF THE PREFERRED EMBODIMENTS OF THE PRESENT INVENTION

Figure 1:
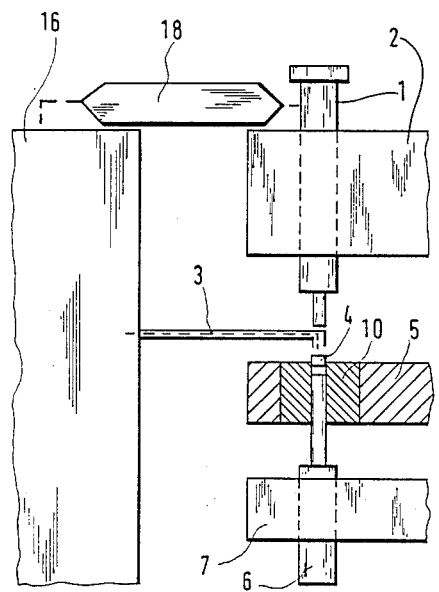
FIG. 1 is a partial cross-sectional side view of a first embodiment of the present invention.

FIG. 1 shows a diagrammatic representation of the system according to the invention, in which a laser 16 is arranged on a tablet-producing press and is functionally connected to it via a synchronizing component 18. The tablet-producing press is provided with a mobile upper punch 1 running in an upper punch guide 2, a mobile lower punch 6 running in a lower punch guide 7, between which is located the die table 5 with a die 10. Shown diagramatically inside the die is a molded item 4, to which the laser beam 3 produced by the laser 16 is directed, in order to effect a marking generally coterminously with ejection of the molded item 4 from the matrix 10.

Figure 2:
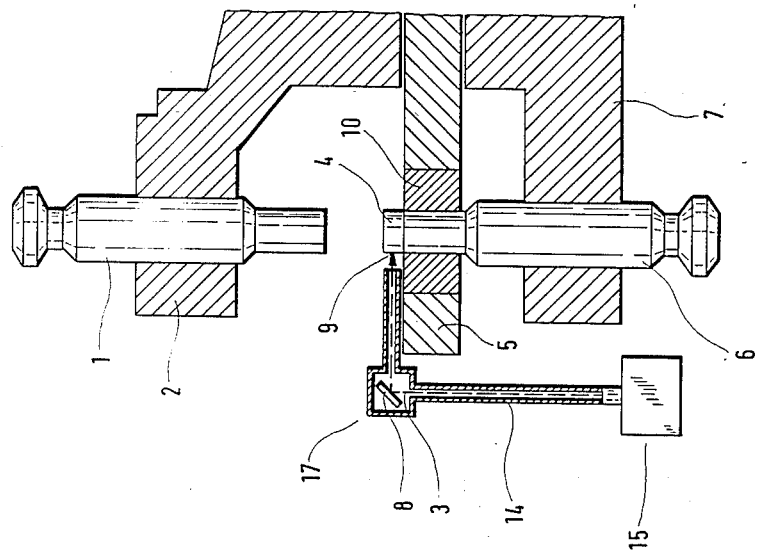
FIG. 2 is a partial cross-sectional side view of a second embodiment of the present invention.
Figure 3:
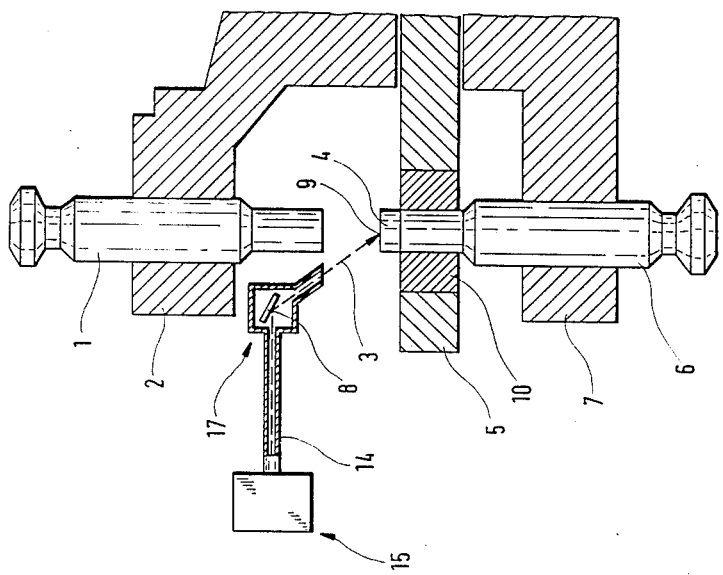
FIG. 3 is a partial cross-sectional side view of a third embodiment of the present invention.

FIGS. 2 and 3 show the arrangement of an optical system 15, provided with a plurality of interchangeable marking masks, in the laser beam 3, which by means of a mirror 8 in the beam deflection system 17 is directed onto the molded item 4, in order to carry out the marking 9 at the very moment that the molded item 4 is ejected from the die 10 of a rotary press of conventional design the lower punch 6 moving in the punch guide 7. The tablet-producing press is provided on a circular track of the die disk 5 with a number of dies 10, in which the lower punch 6 and the upper punch 1 running in the upper punch guide 2 engage, in order to form the molded item 4. For safety reasons, the laser beam 3 runs inside protective tubes 14. The laser beam 3 is generated by a laser 16, not shown in the figures, arranged on the tablet-producing press. In FIG. 2, the deflection system 17 is located next to the die disk, in order to direct the laser 16, either from below if the laser is arranged beneath the die disk 5, as shown, or from above if the laser is arranged above the die disk 5 (not shown), onto the side edge of the molded item 4, so that a marking 9 is produced on the edge of the molded item 4.

In FIG. 3 the laser is arranged to the side above the die disk 5, and the deflection system 17 with the mirror 8 is arranged directly next to the upper punch 1, so that the laser beam 3 strikes the top of the molded item 4 at the moment of ejection from the die or, as the case may be, also immediately prior thereto, and produces a marking 9 at that location.

In order to apply different markings, the optical system 15 is designed so that marking masks with openings in the form of the desired marking can be arranged in the laser beam 3. When the product is changed, only a change of the marking mask is required.

Figure 5:
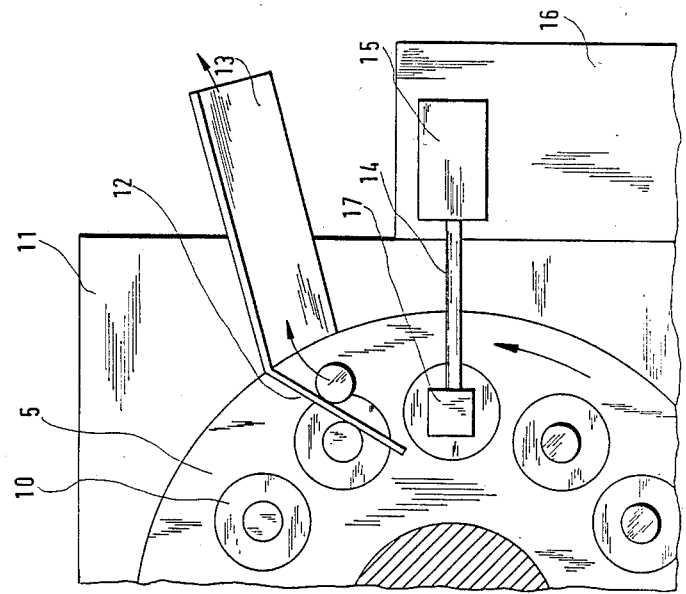
FIG. 5 is a top view of the first embodiment of the present invention.
Figure 4:
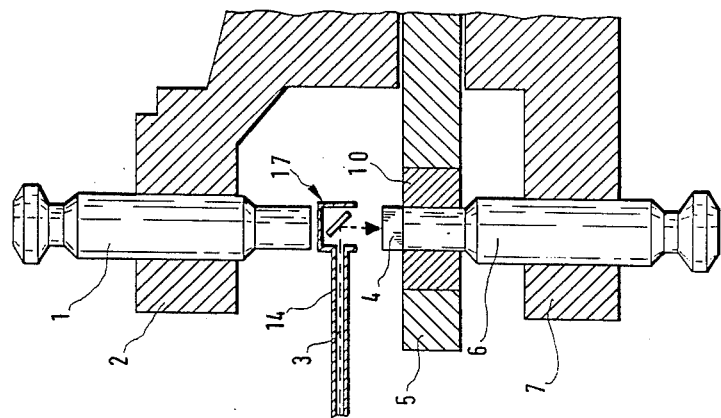
FIG. 4 is a partial cross-sectional side view of the first embodiment of the invention.

FIGS. 4 and 5 show the device for marking tablets or molded items according to the invention in the form of a rotary tablet-producing press, the laser 16 being arranged next to the body of the machine 11 and having an optical system 15 such that the laser beam 3 runs in the protective tube 14 parallel to the surface of the die disk 5 at a distance from the surface. The deflection system 17 with its mirror 8, which is located at the end of the protective tube 14, is placed in the circuit of the dies 10 above a stop position of the die 10 after the pressing process, but before the ejection of the molded item 13. This has the advantage that marking can take place on the entire surface of the molded item 4, and the deflection system 17 and pressing tools, through being arranged at different locations on the circuit of the die 10, within the die disk 5, do not spatially interfere, and facilitate the subsequent fitting out of existing presses 16 with the optical system 15 and deflection system 17, the pressing tools being the mobile upper punch running in the guide 2 and the mobile lower punch running in the guide 7, which engage in the die 10.

Figure 8:
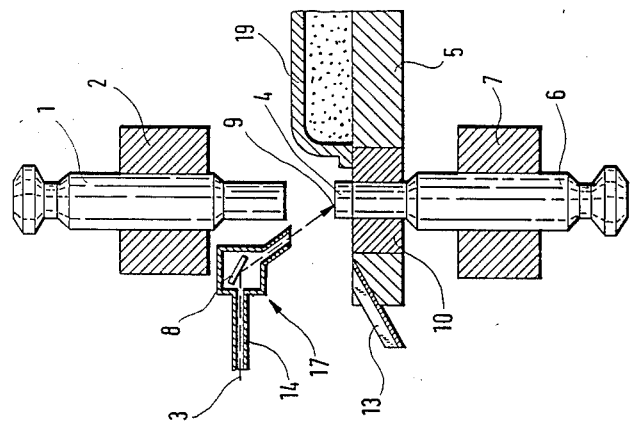
FIG. 8 is a partial cross-sectional side view of a sixth embodiment of the present invention.
Figure 7:
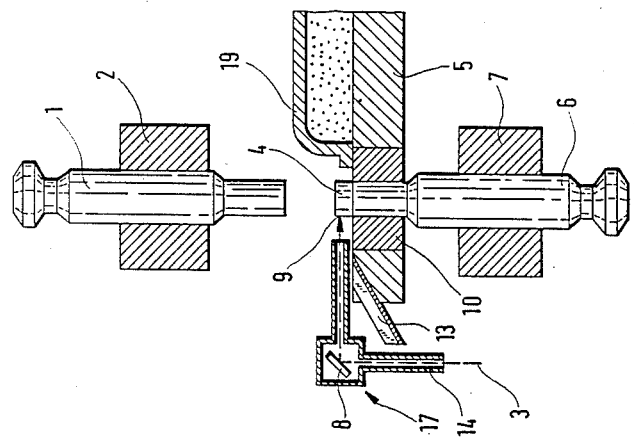
FIG. 7 is a partial cross-sectional side view of a fifth embodiment of the present invention.
Figure 6:
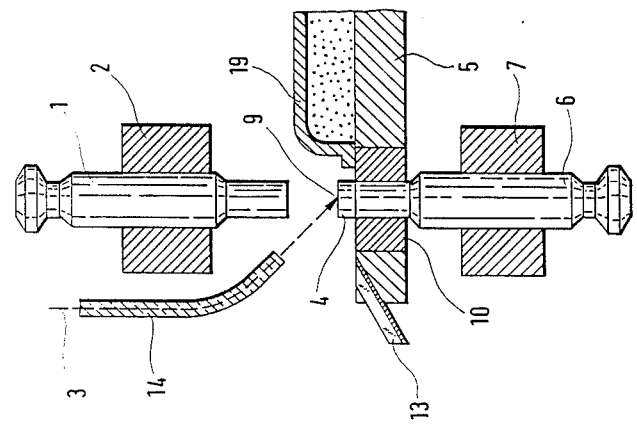
FIG. 6 is a partial cross-sectional side view of a fourth embodiment of the present invention.
Figure 10:
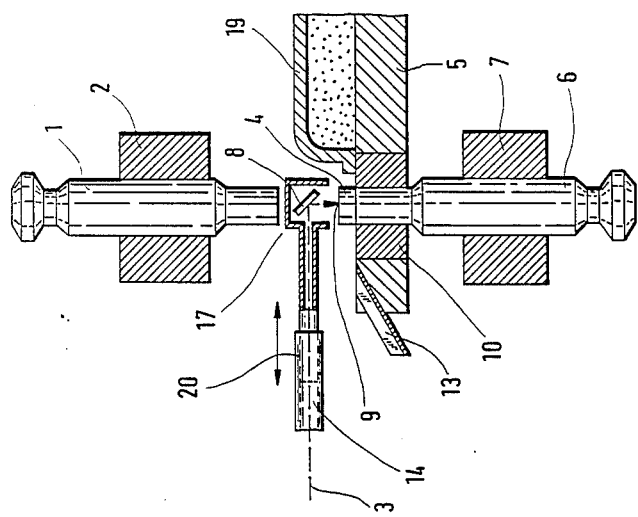
FIG. 10 is a partial cross-sectional side view of the seventh embodiment of the present invention.
Figure 9:
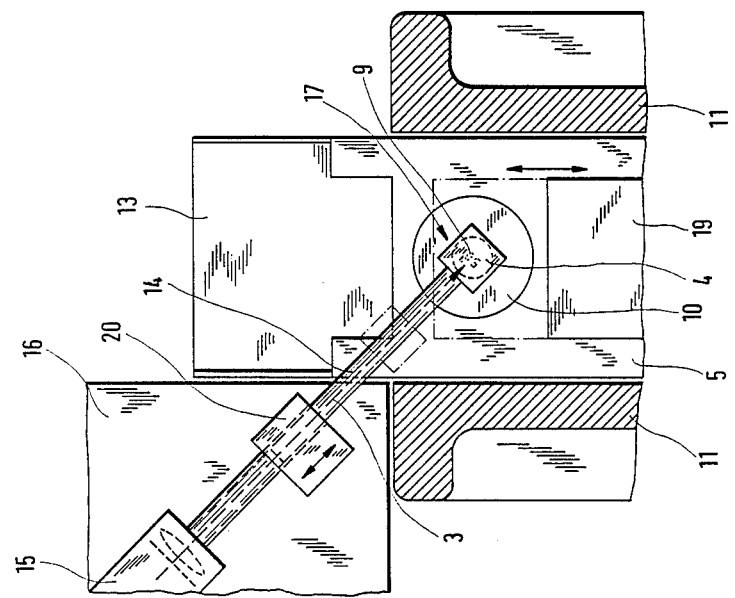
FIG. 9 is a plan view of a seventh embodiment of the present invention.

However, the design according to the invention can also be embodied with so-called eccentric presses. The arrangement of laser 16, optical system 15 and, as the case may be, deflection system 17 is represented diagramatically in FIGS. 6 to 10. A known design of an eccentric press includes within the body of the machine 11 a die 10 located in the die table 5, in which during the pressing process the upper punch 1 and lower punch 6 engage to form a molded item 4. Punches 1 and 6 run back and forth in guides 2 and 7. The filling of the die 10 with material is done via a filler 19 which is displaceable on the surface of the die table 5, and, at the same time, conveys sideways to the ejecting device 13 arranged at an angle on the edge of the die table 5 the molded item 4 ejected from the die 10 by the lower punch 6. Upon return of the filler, the press is prepared for the next pressing process. With eccentric presses it is particularly advantageous to use optical glass fibers with an appropriate optical system as protective tubes 14 for guiding the laser beam 3, as shown in FIG. 6. The mobility of the glass fibers makes possible an arrangement of the end of the glass fiber optics immediately next to the upper punch 1 in such a way that the laser beam strikes the top of the molded item 4 to produce a marking 9. Alternatively, it is also possible, as shown in FIG. 8, to arrange a deflection system 17 with a mirror 8 next to the upper punch, in order to direct the laser beam 3 onto the top of the molded item 9, when the latter is ejected from the die 10 by the lower punch 6. However, it is also possible, as shown in FIG. 7, to arrange the deflection system 17 with mirror 8 at the side of the guide table 5 a little above the surface, so that the laser beam 3 strikes the side edge of the molded item 4 and produces a marking 9 on its edge. It is also possible in principle, by designing the deflection system 17 to move back and forth, to bring it cyclically into a position beneath the upper punch 1 above the molded item 4, so that the laser beam 3 strikes the molded item 4 vertically from above, as shown in FIGS. 9 and 10. Given appropriate synchronization of the movements of upper punch 1, lower punch 6 and deflection system 17, the laser beam marking of the molded item 4 can take place still within the die 10, but also during the ejection process, as long as the molded item is still located beneath the deflection system 17 moved into its marking position, or in the area of the laser beam 3. The mobility of the deflection system 17 can be achieved, for example, using protective tubes 14, which are telescopically displaceable into one another and which are moved synchronously with the operating cycles of the press by means of an appropriate system not shown in the Figures.

FIG. 9 shows a plan view and FIG. 10 a sectional view of such an embodiment of the design of an eccentric press.

Figure 11:
FIG. 11 is a photograph of a tablet marked in accordance with the present invention.

FIG. 11 is a photograph of a tablet marked according to the invention on the top with two numbers, and it shows that depressions are produced in the surface by the laser beam, which represent visible and legible markings.

Example

Preparation of placebo cores for markings with $CO_2$-laser

In principle, a number of positions in the tablet-producing machine are suitable for the laser marking of tablets. In this case, the position was chosen where the tablets are still located in the die of the rotary plate, directly before ejection from the die. The synchronization of the laser pulses was produced by electronic connection between the tablet-producing press and the laser.

1. Composition

| Raw Material | per core | per lot, 10 kg = 30,300 cores weighing 330.0 mg each |
|---|---|---|
| 1. Lactose D 80 Ph.Eur II | 80.00 mg | 8,000.00 g |
| 2. Maize starch Ph.Eur.I | 10.00 mg | 1,000.00 g |
| 3. Gelatine DAB 8 | 3.00 mg | 300.00 g |
| 4. Distilled water | 27.00 mg | 2,700.00 g |
| 5. Maize starch Ph.Eur.I | 6.00 mg | 600.00 g |
| 6. Magnesium stearate | 1.00 mg | 100.00 g |

| Raw Material | per core | per lot, 10 kg = 30,300 cores weighing 330.0 mg each |
|---|---|---|
| Ph.Eur.II | | |

2. Preparation procedure 8,000.0 g of lactose D 80 and 1,000.0 g of maize starch are sieved with a 1.0 mm Frewitt sieve and then granulated with the warm solution of 300.0 g gelatine in 2,700.0 g water in a WSG UD 5 fluidized-bed granulator at an inlet air temperature of about 50°–60° C. After subsequent sieving with a 1 mm sieve, the granular material produced is mixed with a proportionately calculated amount of maize starch and magnesium stearate. The pressing mixture thus obtained is pressed with the aid of the Horn RP 16 H tablet-producing press into tablets having the following parameters:

| | |
|---|---|
| tablet weight | 330.0 mg |
| tablet diameter | 10.5 mm |
| tablet radius of curvature | 9.5 mm |
| appearance | round biconvex film tablet cores |
| color | white |
| disintegration time (in $H_2O$) | about 10 mins. |
| friability | max. 0.3% after 10 min. |
| tablet hardness | about 80 N |

3. Marking

Directly after being pressed, the tablets were marked in the tablet-producing machine with the aid of a $CO^2$ (sic) laser. The marking was applied in the form of the number "56" in the outer layer of the surface of the tablet. During the process, the tablet-producing machine took on the function of an alignment device.

I claim:

1. A process for applying markings or break notches on molded items or tablets, said process comprising:
   treating a surface of a molded item or tablet with a laser beam, said treatment being generally coterminous with ejection of the molded item or tablet from a die of a press.

2. The process for applying markings or break notches on molded items or tablets as claimed in claim 1, further including deflecting said laser beam onto the top of said molded item or tablet.

3. A device for applying markings or break notches on molded items or tablets by means of a laser beam, comprising:
   an installation which generates a laser beam, said installation for generating the laser beam being arranged on a tablet-producing press and being connected to said tablet-producing press by a synchronization system; and
   a deflection system arranged on a die support of said tablet-producing press to deflect said laser beam onto the surface of the molded item or tablet.

4. The device for providing markings or break notches on molded items or tablets as claimed in claim 3, wherein said installation for generating said laser beam is a gas laser.

5. The device for applying markings or break notches on molded items or tablets as claimed in claim 3, wherein said installation for generating said laser beam is provided with an optical system including a plurality of interchangeable masks, said interchangeable masks including openings through which said laser beam passes.

6. The device for applying markings or break notches on molded items or tablets as claimed in claim 3, wherein said deflection system is arranged and aligned at the side of said die support such that said laser beam runs parallel to the surface of said die support towards a vertical axis of a die.

7. The device for applying markings or break notches on molded items or tablets as claimed in claim 3, wherein said deflection system is arranged and aligned at the side of an upper punch of said tablet-producing press such that said laser beam strikes the top of said molded item or tablet before the center of the molded item or tablet has been displaced horizontally from a vertical axis of a die.

8. The device as claimed in claim 3, including systems to move said deflection system between a position at the side of an upper punch and a position above a die.

9. A process for applying markings or break notches on molded items or tablets by treating a surface of a molded item or a tablet with a laser beam, said process comprising:
   deflecting said laser beam onto the side face of the molded item or tablet, said treatment being generally coterminous with ejection of said molded item or tablet from a die of a press, said treatment occurring when the molded item or tablet is ejected above the upper edge of the die by a lower punch.

10. A process for applying markings or break notches on molded items or tablets, comprising:
    treating a surface of a molded item or tablet with a laser beam, said treatment being generally coterminous with ejection of the molded item or tablet from a die of a press;
    wherein the shape of said marking or break notch is produced by a marking mask arranged in the path of the laser beam, said marking mask having openings in the shape of the desired marking or break notch.

* * * * *